United States Patent [19]

McCurdy et al.

[11] Patent Number: 5,520,932
[45] Date of Patent: May 28, 1996

[54] FINE-MILLED COLESTIPOL HYDROCHLORIDE

[75] Inventors: Vincent E. McCurdy, Vicksburg; Charles H. Spilman, Kalamazoo, both of Mich.

[73] Assignee: The Upjohn Company, Kalamazoo, Mich.

[21] Appl. No.: 289,321

[22] Filed: Aug. 3, 1994

Related U.S. Application Data

[63] Continuation of Ser. No. 956,429, Oct. 1, 1992, which is a continuation of Ser. No. 623,904, Filed as PCT/US89/02187, May 24, 1989, abandoned, which is a continuation-in-part of Ser. No. 211,373, Jun. 24, 1988, abandoned.

[51] Int. Cl.$^6$ ........................................ A61K 9/14
[52] U.S. Cl. .................. 424/501; 424/439; 424/440; 424/452; 424/465; 514/952; 264/140
[58] Field of Search ............................ 424/440, 78.38, 424/501, 469–470, 78.12; 521/34; 519/952; 264/140

[56] References Cited

U.S. PATENT DOCUMENTS

| | | | |
|---|---|---|---|
| 3,692,895 | 9/1972 | Nelson et al. | 424/78 |
| 3,803,237 | 4/1974 | Lednicer et al. | 260/584 R |
| 3,846,541 | 11/1974 | Howard | 424/79 |
| 4,404,346 | 9/1983 | Pirotta et al. | 424/79 |
| 4,439,419 | 3/1984 | Vecchio | 424/78 |
| 4,631,305 | 12/1986 | Guyer et al. | 523/400 |
| 4,814,354 | 3/1989 | Ghebre-Sellassie | 424/440 |
| 4,917,309 | 4/1990 | Zander et al. | 241/5 |
| 5,174,512 | 12/1992 | Orlandi | 241/72 |

FOREIGN PATENT DOCUMENTS

| | | |
|---|---|---|
| 0026574 | 8/1980 | European Pat. Off. . |
| 1238597 | 6/1969 | United Kingdom . |

OTHER PUBLICATIONS

Physician's Desk Reference (PDR), 42nd Edition, pp. 2115–2116, 1988.

Grant & Hackh's Chemical Dictionary 5th ed, Pub. McGraw–Hill p. 370.

*Primary Examiner*—Edward J. Webman
*Attorney, Agent, or Firm*—Martha A. Gammill

[57] ABSTRACT

The present invention provides a novel fine milled form of a known pharmaceutical composition, colestipol hydrochloride. This fine milled form of colestipol hydrochloride yields pharmaceutically elegant dosage forms exhibiting increased potency, including non-gritty oral powders and high dose oral tablets (e.g., 1000 mg tablets). Conventional colestipol hydrochloride was heretofore available in spherical granules which produced less elegant (gritty) oral suspensions and oral tablets with substantially lower doses of drug (e.g., ca 500 mg).

3 Claims, No Drawings

FINE-MILLED COLESTIPOL HYDROCHLORIDE

The present application is a continuation application of U.S. Ser. No. 07/956,429, filed 1 Oct. 1992; which is a continuation application of U.S. Ser. No. 07/623,904, filed 19 Dec. 1990, now abandoned; which is the national stage of international application PCT/US89/02187, filed 24 May 1989, which designated the U.S., now abandoned; which is a continuation-in-part of U.S. Ser. No. 07/211,373, filed 24 Jun. 1988, now abandoned.

BACKGROUND OF THE INVENTION

The present invention provides a novel composition of matter, novel formulations containing it, novel methods for using it, and a novel process for making it. In particular, the present invention provides substantially uniformly small, pharmaceutically elegant particles of colestipol hydrochloride, pharmaceutical compositions containing them, and methods for using them to treat hypercholesterolemia in humans. These pharmaceutical compositions include tablets (particularly tablets containing greater than 500 mg of drug), palatable or non-gritty oral suspensions or powders (flavored or unflavored), and various drug-containing food products having improved palatability.

Colestipol is a basic anion exchange resin described as a high molecular weight copolymer of diethylenetriamine and 1-chloro-2,3-epoxypropane (hydrochloride), with approximately 1 out of 5 amine nitrogens protonated. It is a light yellow resin which is hygroscopic and swells when placed in water or aqueous fluids. See Merck Index (Tenth Edition) #2440, page 2438. Colestipol hydrochloride is commercially available in granule form as COLESTID® Granules. See Physicians Desk Reference (PDR) 42nd Ed., p. 2119 (1988).

COLESTID® Granules are marketed as a hyperlipidemia agent for oral use. COLESTID® Granules are tasteless and odorless, although they may have a pronounced gritty texture when suspended in liquids consumed orally.

Cholesterol is the major, and probably the sole precursor of bile acids. During normal digestion, bile acids are secreted via the bile from the liver and gall bladder into the intestines. Bile acids emulsify the fat and lipid materials present in food, thus facilitating absorption. A major portion of the bile acids secreted is reabsorbed from the intestines and returned via the portal circulation to the liver, thus completing an enterohepatic cycle. Only very small amounts of bile acids are found in normal serum. Physicians' Desk Reference (P.D.R.) 42nd Edition, 1988, page 2115.

Colestipol hydrochloride, e.g., COLESTID® Granules, is indicated as adjunctive therapy to diet for the reduction of elevated serum cholesterol in patients with primary hypercholesterolemia (elevated low density lipoproteins).

Heretofore the only known form of colestipol hydrochloride was the granulated form, specifically COLESTID® Granules, which consist of spherical beads of colestipol hydrochloride wherein at least 75% of the particles by weight or volume are greater than 100 microns in diameter and at least 30% of the particles are greater than 80 microns in diameter. These granules must be consumed orally and typically require admixture with a pleasant tasting vehicle at the time of oral consumption. COLESTID® Granules are greater than 99.5% colestipol hydrochloride by weight. The typical daily dose of COLESTID Granules employed for anti-hyperocholesterolemia varies from 15 to 30 grams per day. Patients taking this medication ordinarily must continue to take anti-cholesterolemic drugs throughout their lives to maintain reduced serum cholesterol levels.

The heretofore known form of colestipol hydrochloride, i.e., COLESTID® Granules, is not well tolerated by patients since the gritty texture of the product is objectionable, severely compromising the pharmaceutical elegance and patient acceptance. Further, the use of a granule formulation means that drug must be mixed with a liquid vehicle at the time of consumption, an inconvenience for many patients. For example, in order to take this drug, patients must measure the powder, disperse it in a liquid vehicle and drink the entire contents. A pharmaceutically more elegant and convenient dosage form would be a tablet or capsule product. However, ingestion of an unacceptably large number of tablets would be necessary to make the ingestion of colestipol hydrochloride in a tablet dosage form practical. Capsules are physically capable of handling no more than 600 mg of the colestipol hydrochloride. Moreover, the colestipol hydrochloride granules as presently available cannot be tableted in strengths greater than 600 mg without making an unacceptably large-sized tablet.

Heretofore no colestipol hydrochloride has had sufficient pharmaceutical elegance and efficacy to provide patients with a fully convenient and effective drug.

INFORMATION DISCLOSURE

Colestipol hydrochloride in the form of spherical beads, wherein at least 75% of the particles by weight or volume are greater than 100 microns in diameter and 30% of the particles by weight or volume are greater than 80 microns in diameter, is known. See PDR, supra, page 2115. The use of oral colestipol hydrochloride formulations in spherical bead form to treat hypercholesterolemia is also known. See, e.g., U.S. Pat. No. 3,692,895.

U.S. Pat. No. 4,404,346 discloses and claims a process for reducing the size of particles of anti-hypercholesterolemic cholestyramine resins. Powdered cholestyramine resin is produced by swelling or shrinking resin particles by contact with water or an organic solvent to introduce strain within the particles and comminuting the swollen or shrunk particles by grinding them in a rotary attrition mill. Particle sizes such that 90% by weight and/or number is below 30 microns in average particle diameter in the wet swollen state are reported to have been achieved.

EP-B-0026574, claims a process for reducing the size of particles of synthetic polymeric ion exchange or adsorbent resins in general, and of cholestyramine specifically. It also claims the comminuted synthetic polymeric ion exchange or adsorbent resin obtained by this process, the comminuted cholestyramine obtained by this process, and the resins themselves in pharmaceutical formulations.

U.S. Pat. No. 3,692,895 claims a method of using colestipol hydrochloride to reduce hypercholesterolemia in humans. It discloses compositions (including tablets and capsules) and processes for reducing hypercholesterolemia in affected mammals and birds. The compositions and processes utilize an orally effective amount of a non-toxic polymer prepared from a polyethylenepolyamine such as tetraethylenepentamine and a bifunctional substance such as epichlorohydrin or 1,2:3,4-diepoxybutane.

U.S. Pat. No. 4,439,419 discloses a method of using colestipol hydrochloride to neutralize gastric acidity and treat hyperacidity in humans having an excess of gastric acidity and the treatment of ulcers.

A preferred method for preparing colestipol hydrochloride for medical use is disclosed in U.S. Pat. No. 3,803,237 and is known as the "bead process." U.S. Pat. No. 4,631,305 claims compressed tablets containing a polymeric material such as colestipol hydrochloride as a tablet disintegrating agent.

The use of a precise incremental cutting action mill (e.g., a COMITROL® 1700 Mill) for micronizing (particle size reduction) of certain pharmaceutical products is known, but such mills have never been employed for wet milling of products such as colestipol hydrochloride.

SUMMARY OF THE INVENTION

The present invention particularly provides:

(1) a composition of matter consisting essentially of fine milled colestipol hydrochloride (FMCH);

(2) FMCH wherein greater than 95% of the particles are non-spherical, fractured particles, greater than 75% of the particles (by weight or volume) are smaller than almost 65 microns in diameter and greater than 30% of the particles (by weight or volume) are less than about 30 microns in diameter;

(3) FMCH in a pharmaceutical unit dosage form;

(4) FMCH in tablet, or capsule form;

(5) FMCH in tablet containing about 1 gm of drug;

(6) in the method of treating hypercholesterolemia in a patient by administering a pharmaceutical composition containing colestipol hydrochloride, the improvement characterized by use of fine milled colestipol hydrochloride in said composition;

(7) the above improvement wherein a known cholesterol-lowering agent, such as a 3-hydroxy-3-methylglutaryl coenzyme A reductase inhibitor or gemfibrozil (LOPID) is administered concomitantly; and (8) a food product containing a concentration of FMCH effective to treat hypercholesterolemia when a predetermined quantity of said product is consumed.

The invention thus provides a new physical form of colestipol hydrochloride, namely fine-milled colestipol hydrochloride, which is ideally suited for the formulation of elegant pharmaceutical and food delivery systems. The fine particle size colestipol hydrochloride enables the production of palatable, non-gritty dispensable oral suspensions, dispensable powders (flavored or unflavored), food products and high dose tablets.

By "fine-milled" is meant a substantially non-spherical form of colestipol hydrochloride (greater than 95% non-spherical, fractured particles, most preferably greater than about 99% non-spherical fractured particles) wherein greater than 75% of the particles by weight or volume are less than about 100 microns in diameter; more preferably greater than about 75% of the particles, by weight or volume, are less than about 65 microns in diameter and greater than about 30% of the particles (as a proportion of their total weight or volume), are less than about 30 microns in diameter. These measurements of diameter of particle size may be made by standard light scattering assay techniques.

By "pharmaceutical unit dose" is meant a discrete quantity of FMCH in a form suitable for administering for medical purposes. Thus, an ideal unit dose would be one wherein one unit, or an integral amount thereof (e.g., one or more packets each containing a predetermined amount of FMCH) contains a safe and effective dose for lowering serum cholesterol. As would be apparent to a person of ordinary skill in pharmaceutical formulations, the fine-milled colestipol hydrochloride of the present invention can be formulated into conventional tablets for oral administration, optionally utilizing known tablet excipients, e.g., binders, fillers, and the like.

The fine-milled colestipol hydrochloride of this invention is most preferably prepared by mixing conventional colestipol hydrochloride granules (e.g., spherical beads) with a quantity of water that is at least 5 times the weight of the colestipol hydrochloride. Once mixed, the suspension is passed through a precision incremental cutting machine set up with a microcut head as described below. The water-drug suspension is pumped into the machine at a rate that does not exceed the limitations of the machine. After discharge, the suspension is collected and the water is removed by isolating the solids through centrifugation or sedimentation followed by a drying operation. The discharge can be dried directly by spray drying or tray drying.

The dried solids thus prepared typically form aggregates of FMCH. These aggregates can be disrupted by most any common dry milling equipment, such as a rotary attrition mill or a ball mill. The aggregates can also be disrupted by using the precise incremental cutting machine. Disruption of aggregates results in substantial reduction in apparent particle size of the FMCH during the dry milling operation. The dry milling operation affects only the size of the dried aggregates, i.e., apparent particle size. Moreover, the aggregates readily disperse when rehydrated.

The FMCH produced by the above process results in a free-flowing powder consisting of a mixture of discrete particles and aggregates of particles, if not disrupted as described above. Microscopic examination of these particles shows that the particles are irregular-shaped. When produced using the cutting tolerances described below, essentially all particles range in size from 30–65 microns. Typically less than 1% resemble the conventional spherical beads of the starting material. FMCH powder is ideally suited for incorporation into a number of pharmaceutical dosage forms and food products. For example, FMCH is used to produce high dose oral tablets (i.e., up to 1000 mg) with minimal excipient levels. The conventional spherical beads, although capable of being tableted, can only be acceptably prepared, in lower dose tablets e.g., about 600 mg or less, because tablets of substantially higher dosage are physically too large to be ingested whole.

Surprisingly and unexpectedly, the novel form of colestipol hydrochloride of the present invention is more potent than the conventional spherical beads of the prior art, allowing for more convenient oral administration, utilizing less frequent and/or lower doses of the drug. In conventional biological tests in quail, FMCH was found to be approximately 2.7 times more potent at lowering beta-cholesterol than conventional colestipol hydrochloride granules. Moreover, because this increased potency is coupled with the ability to produce high dose oral tablets, the present invention provides a surprisingly and unexpectedly more elegant and convenient pharmaceutical product.

Thus, in hyperlipidemic patients with serum cholesterol values above 200 mg per 100 ml, the composition of the present invention effectively lowers cholesterol levels when the daily dose of FMCH varies from about 3 to about 12 gm, administered from one to three times daily. Unexpectedly, therefore, the present invention provides the opportunity for conveniently dosing a patient with 1–4 high (e.g., 1 gm) dose tablets before each meal.

FMCH can be combined with other known cholesterol lowering agents to provide further lowering of serum cholesterol, triglyceride, and LDL cholesterol values. Such agents include, e.g., MEVACOR®, niacin, LOPID® or LORELCO®.

The FMCH is adaptable to making a flavored dry mix which is constituted into a flavored beverage by simply adding water. These flavored mixes typically contain a viscosity inducing agent such as a gum or a low molecular weight synthetic polymer; flavoring agents such as sucrose, aspartame or sodium saccharin; colorants; wetting agents or surfactants such as dioctyl sodium sulfosuccinate or sodium lauryl sulfate; agents to provide tartness and control acidity such as citric acid, ascorbic acid, potassium citrate or sodium citrate; flavorants such as lemon or orange; and preservatives such as BHA. Similarly, it can be used as an additive to powdered food products, including pudding and pie filling mixes, gelatin, cake mixes, powdered eggs and powdered potatoes, instant breakfast drinks, gravies and sauces (e.g., Hollandaise), prepared cereal products (oatmeal, cream of wheat, hominy grits), and drink mixes (powdered fruit punches, powdered fruit drinks). Likewise, FMCH can be used in prepared foods themselves; for example, it can be used as an additive in cakes, pasta products, candy, cookies, confections, yogurts, including frozen yogurt products, ice cream and ice cream products and prepared meats (hamburger, sausages and the like).

In order to successfully produce a colestipol hydrochloride suitable for each of the various purposes set forth above, essentially all (most preferable more than 99%) of the spherical bead starting material must be fractured. Unexpectedly, however, conventional milling techniques, e.g., particularly and especially those used in the prior art for milling anti-hypercholesterolemic resins fail to yield FMCH as described herein. Accordingly, the present invention further provides a surprising and unexpected method of preparing FMCH that contains little or no residual spherical bead starting material. In contrast, conventional milling operations yield an unacceptable mixture of partially milled colestipol hydrochloride and unmilled colestipol hydrochloride which exhibit unacceptable texture and gritty taste when ingested orally and/or fail to yield acceptable high dose (ca. 1000 mg) tablets.

For example, conventional wet and dry milling operations fail to reduce the particle size of colestipol hydrochloride. Conventional dry milling colestipol hydrochloride results in no particle size reduction. Colestipol hydrochloride actually degrades or damages milling apparatus before any particle size reduction takes place. Conventional wet milling in a ball mill or homogenizer similarly results in no particle size reduction. Wet milling performed in a rotary attrition mill (see U.S. Pat. No. 4,404,346) results in inadequate particle size reduction. The colestipol hydrochloride still retains a gritty texture when ingested. Similarly, inadequate particle size reduction can take place when colestipol hydrochloride is wet milled with a hammer mill such as the Mikropulverizer. The resultant milled resin contains a mixture of intact beads, fractured beads and aggregates of fractured beads. The mechanism of particle size reduction in the Mikropulverizer results in random particle movement and a wide bimodal distribution in particle size of product. Moreover, the Mikropulverizer is not suitable for a well-controlled fine grinding process. The screens themselves are made of a relatively soft metal composition which is prone to deformation and wear with time. The screen with the smallest opening has only a 0.01 inch slotted opening. The distance between the hammer and the screen is variable and wide, ca. 0.100 inch. Colestipol hydrochloride wet milled with the Mikropulverizer was unacceptable from a palatability viewpoint because of the intact beads after wet milling.

The only milling method found suitable for the production of FMCH as claimed herein is a wet milling process with the Comitrol 1700 mill configured with a 222084 microcut head. After the wet milled drug is dried, it may be dry sized with various equipment to yield either a bi-modal mixture of particle aggregates and primary particles or a uni-modal mixture of discrete primary particles. The differences between this "precise incremental cutting action machine" (Comitrol) and a hammer mill (Mikropulverizer) mill are well known to those of ordinary skill in pharmaceutical manufacturing techniques and are summarized below:

1. The Comitrol is a machine which reduces particle size by a cutting mechanism. The Mikropulverizer is a machine which reduces particle size by impact and attrition mechanisms. On this basis alone, these are very different machines.

2. The Comitrol has been machined to extremely tight tolerances so that a blade gap setting of 0.0009 inch (0.0023 cm) and a distance of 0.001 inch (0.0025 cm) between the rotating tip and blade face are achievable. The narrow blade gap setting means that a particle must have at least one dimension that is 23 microns or smaller to exit the cutting chamber. The Mikropulverizer is machined to much more "relaxed" tolerances.

3. Particle size reduction in the Comitrol occurs in well controlled manner, i.e., each particle passes through a similar path prior to leaving the milling chamber. Particle size reduction in the Mikropulverizer occurs more randomly, i.e., particles pass through very different paths as demonstrated by the fact that many of the particles do not even fracture.

When the Comitrol 1700 mill is outfitted with a 222084 microcut head, it is capable of wet milling colestipol hydrochloride at a high production output, the equivalent of 1500 grams of dry colestipol hydrochloride per minute. Wet milling colestipol hydrochloride with the Comitrol 1700 mill will be successful with a water:drug ratio greater than 4:1. However, a water:drug ratio of approximately 12:1 appears to be the optimal ratio for maximal production output. The input feed rate of colestipol hydrochloride suspended in water has also been determined to have no effect on the particle size of the milled colestipol hydrochloride.

The subsequent dry milling of FMCH affects the size of the FMCH aggregates formed after dry milling. A mill with an impact mechanism of size reduction substantially deaggregates FMCH. Dry milling also affects the bulk density of the milled powder. Colestipol hydrochloride that has been wet milled and deaggregated during dry milling, has a higher bulk volume than colestipol hydrochloride that has been wet milled and not deaggregated.

The wet milling operation does not affect the in-vitro cholate binding capacity of colestipol hydrochloride. Decreasing the water:drug ratio during wet milling increases the fraction of water soluble material (e.g. "impurities") in the milled drug. Thus, surprisingly and unexpectedly, the process of the present invention provides a unique means of producing FMCH suitable for the purposes described herein.

DESCRIPTION OF THE PREFERRED EMBODIMENTS

EXAMPLE 1 1000 mg FMCH Compressed Tablet

The following 1000 mg compressed tablet is pharmaceutically elegant, e.g., easy to swallow, retains the mechanical strength to resist breakage during rough handling, and rapidly disintegrates once it contacts an aqueous medium:

| Ingredient | Amount to Equal mg/dose |
|---|---|
| FMCH | 1000 |
| Hydroxypropylmethylcellulose (HPMC) K100 | 50 |
| Colloidal silicon dioxide | 1.25 |
| Magnesium stearate NF (powder food grade) | 15 |

The FMCH, HPMC and magnesium stearate are mixed. Colloidal silicon dioxide is then prescreened through a #20 mesh screen and added. The resulting powder is mixed. The magnesium stearate is then prescreened through a #20 mesh screen and added to the mixture. The resultant powder is mixed for at least 30 seconds in a high shear mixer. The mixed powder is then compressed on a suitable tablet press to produce tablets which have a final weight of 1066.5 mg. The tablets have the following properties upon testing:

| Property | Result |
|---|---|
| Disintegration time | 6 min, 50 sec |
| In-vitro cholate binding capacity | 1.3 meq/g |
| Hardness | 37.1 scu |
| Friability | 0.4% |
| Thickness | 0.297 in (.754 cm) |

EXAMPLE 2 Optimizing the use of Comitrol Model 1700

The Comitrol 1700 mill is a unique type of particle size reduction machine. Particles to be reduced are guided to the center of a high speed, rotating impellor. The Comitrol Model 1700 mill is designed to run at a fixed impellor rpm of 11,925. The centrifugal force (ca 12000 G's) is generated by high speed rotation of the impellor which moves the incoming particles out toward the impellor tips. Once particles reach the rotating tips of the impellor, they contact the cutting edge of the stationary microcut reduction head. The particles are cut as they are sheared between the rotating tip and the stationary microcut reduction head.

The microcut reduction head, consists of a number of removable blades which are separated by a narrow gap. The more blades present in a microcut head, the more narrow the gap is between the blades. The smaller the gap distance between the microcut blades, the smaller the particles need to be before they can exit the cutting chamber. Thus, discharge particle size is greatly affected by the number of blades (type of microcut head) used to perform an operation. Moreover, this unique design eliminates random particle movement so a highly uniform and reproducible particle size distribution results.

Use of the Comitrol 1700 to fracture and reduce the particle size of colestipol hydrochloride spherical heads requires varying the number of blades, e.g., decreasing the opening distance and increasing the number of blades between the blades in the microcut head to obtain the FMCH with desired properties. In initial experiments, the opening gap distance is varied from 0.0103 in. (0.026 cm) (microcut head=200084-1 with 200 blades) to 0.0009 in. (0.0023 cm) (microcut head=222084 with 222 blades). The ratio of water:drug in these initial experiments is either 5:1 or 10:1. To prepare the wet slurries, the drug is dispersed in the water using a marine type propeller mixer. A microscopic examination of the output is performed to determine if any substantial particle size reduction had occurred. Those samples found to have substantial particle size reduction are tray-dried (70° C. for 24 hours) and ground.

Although some particle attrition occurs when the microcut head was configured with 200, 212 and 216 blades, microscopic examination of the wet milled slurry indicates that the milling process was far from complete. Many intact beads remain when these microcut heads are used. However, when 222 blades (222084) are used, complete bead fracture is accomplished. Few intact beads can be found upon microscopic examination of the wet milled slurry. Photomicrographs showing the difference between colestipol hydrochloride wet milled with a 212084 microcut head and a 222084 microcut head indicates that with the former head, many intact beads remain after milling whereas with the latter head, no intact beads remain after milling, indicative of complete bead fracture.

Visual and microscopic examination of the colestipol hydrochloride that has been wet milled with the 222084 microcut head and dried shows large aggregates of fractured particles. These aggregates are tightly bound and not easily deaggregated with a mortar and pestle. A particle size analysis (see below) performed on a ground (mortar and pestle) sample resulted in a 55.5 micron median particle size with a hi-modal distribution. The hi-modal distribution is due to a single distribution of discrete particles and a second distribution of aggregated particles.

A light scattering assay used to determine particle size utilized ethylene dichloride (non-aqueous solvent) as the dispersion medium. This medium does not interact or result in swelling of the colestipol hydrochloride so that the particle the instrument detects is essentially unchanged from its natural state. Consequently, The assay measures aggregates of particles as a single particle and the particle size determined is actually an apparent "particle size" for milled colestipol hydrochloride.

To break up these aggregates, a sample is passed through a Bantom Mikropulverizer using a 0.046 HB screen to produce a new particle size distribution. The dry sized sample yields a particle size of 39.6 microns with a unimodal distribution. Microscopic examination of these particles showed that there were few large aggregates of particles remaining. These results indicate that the Mikropulverizer has the capability to deaggregate the aggregates during a dry sizing process. Alternatively, these aggregates may be disrupted by using a precise incremental cutting machine, such as the Comitrol 1700.

The effect of the microcut head used to mill dried colestipol hydrochloride that had been wet milled in the Comitrol 1700 is also examined. A lot of wet mixture is prepared at a 10:1 water:drug ratio using a marine type air-driven propeller mixer. The mixture is wet milled using a 222084 microcut head with a controlled (Masterflex pump) throughput rate of 9600 ml of wet mixture per minute. Approximately one-half the wet milled drug is dry sized with the 180084-2 microcut head and the other half dry sized with the 160084-5 microcut head. The material dry sized with the 180084-2 microcut head results in a smaller apparent "particle size" than the drug dry sized with the 160084-5 microcut head:

| Lot | Microcut Head Used for Dry Sizing | Median | Width |
|---|---|---|---|
| P2175-51A | 180084-2 | 48.9 | 2.61 |

| Lot | Microcut Head Used for Dry Sizing | Median | Width |
|---|---|---|---|
| P2175-51B | 160084-5 | 75.6 | 3.29 |

The difference in apparent "particle size" can be attributed to the smaller opening in the 180084-2 microcut head. The size of the primary particles should be about the same for both these lots since they came from the same source lot of wet milled drug.

We claim:

1. A process for preparing fine milled colestipol hydrochloride (FMCH), wherein greater than 95% of the particles are non-spherical, fractured particles, wherein greater than 75% of the particles (by weight or by volume) are less than about 65 microns in diameter and greater than 30% of the particles (by weight or volume) are less than 30 microns in diameter which comprises subjecting wet colestipol hydrochloride, wherein the water:drug ratio is greater than 4:1, to milling with rotating blades set at a gap of about 0.0023 cm and at a distance of about 0.0025 cm between the rotating tip and blade face.

2. The process of claim 1 wherein the milling is performed at an impellor rpm of about 12,000.

3. The process of claim 2 wherein the milling is performed in a precise incremental cutting action machine configured with a microcut reduction head.

* * * * *

UNITED STATES PATENT AND TRADEMARK OFFICE
CERTIFICATE OF CORRECTION

PATENT NO. : 5,520,932
DATED      : May 28, 1996
INVENTOR(S) : Vincent E. McCurdy It is certified that error appears in the above-indentified patent and that said Letters Patent is hereby corrected as shown below:

On the Cover Page, Inventors: "Vincent E. McCurdy and Charles H. Spilman" should read — Vincent E. McCurdy —

At Column 8, line 26, two occurrences "hi-modal" should read —bi-modal—

Signed and Sealed this

Eighteenth Day of August, 1998

Attest:

BRUCE LEHMAN

Attesting Officer

Commissioner of Patents and Trademarks